United States Patent [19]

Coss

[11] Patent Number: 5,498,159
[45] Date of Patent: Mar. 12, 1996

[54] DENTAL TOOL COUPLING FOR DISPOSABLE TOOTH POLISHER

[75] Inventor: Ronald G. Coss, Newport Beach, Calif.

[73] Assignee: Micro Motors, Inc., Santa Ana, Calif.

[21] Appl. No.: 282,971

[22] Filed: Jul. 29, 1994

[51] Int. Cl.[6] ..................................................... A61C 1/08
[52] U.S. Cl. ............................................ 433/126; 433/125
[58] Field of Search ..................................... 433/125, 126, 433/128, 132; 285/276, 277, 304, 317; 403/348, 349

[56] References Cited

U.S. PATENT DOCUMENTS

| | | | |
|---|---|---|---|
| 3,631,597 | 1/1972 | Lieb et al. | 433/126 |
| 4,211,009 | 7/1980 | Leonard | 433/126 |
| 4,403,958 | 9/1983 | Löhn | 433/126 |
| 4,403,959 | 9/1983 | Hatakeyama | 433/126 |
| 4,643,675 | 2/1987 | Kuhn | 433/126 |
| 4,647,081 | 3/1987 | Landgraf et al. | 433/126 |
| 5,234,338 | 8/1993 | Young | 433/126 |

*Primary Examiner*—Cary E. O'Connor
*Attorney, Agent, or Firm*—Knobbe, Martens, Olson & Bear

[57] ABSTRACT

An improved dental tool coupling apparatus for coupling disposable tool heads to drive housings. A tubular nose of the housing receives a tool head shaft, which extends within a tubular output shaft coupled to a drive means. The output shaft includes a plurality of radially disposed sockets containing balls, the balls being biased into an interior space of the tubular output shaft. Upon axial coupling of the disposable tool head to the housing, the tool head shaft inserts within the tubular output shaft so that the balls create a series of axial grooves in the tool head shaft. A circular spring retainer surrounding the output shaft biases the balls into the axial grooves to maintain a certain level of rotational coupling therebetween.

10 Claims, 3 Drawing Sheets

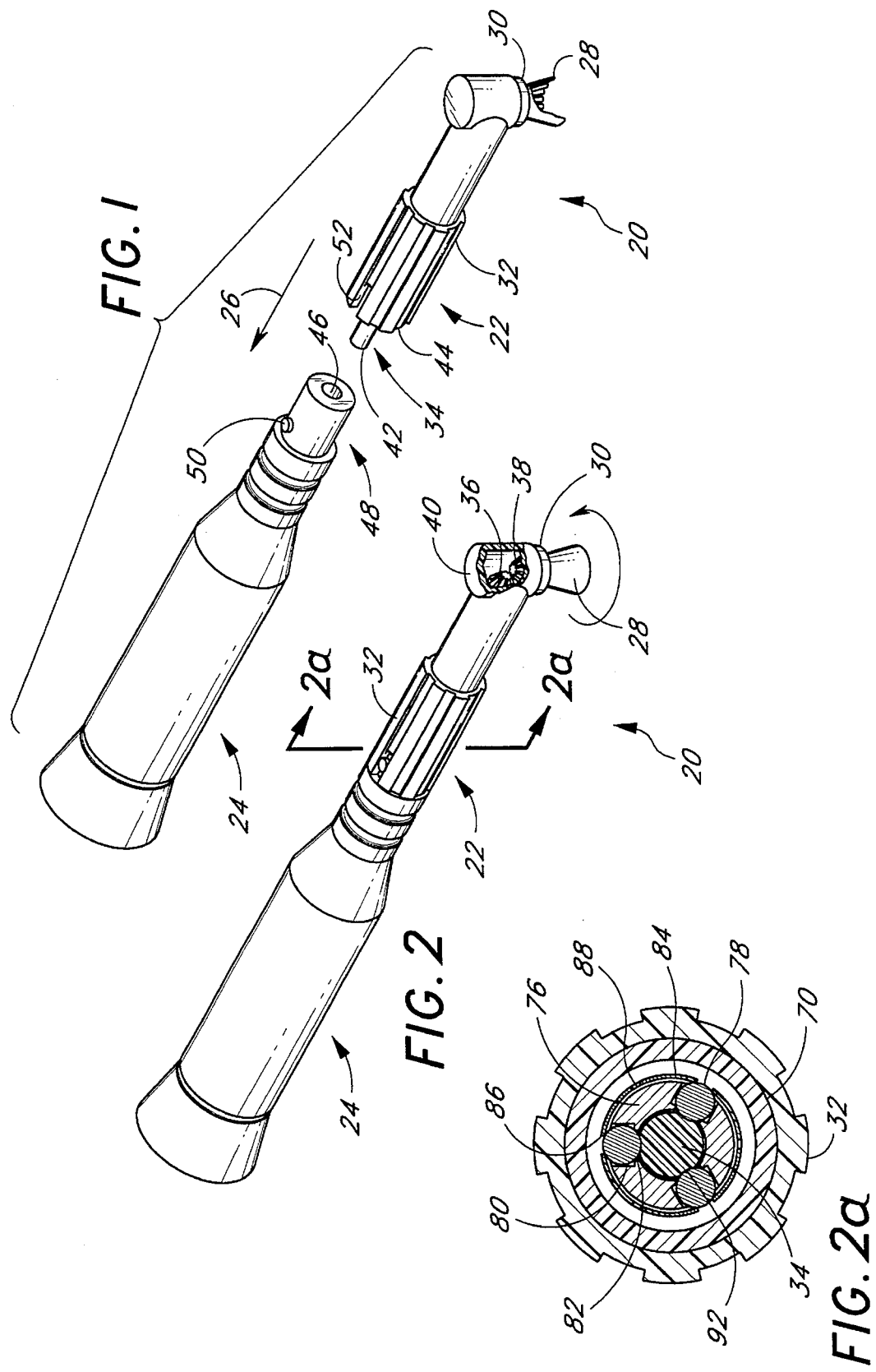

DENTAL TOOL COUPLING FOR DISPOSABLE TOOTH POLISHER

FIELD OF THE INVENTION

This invention relates to dental apparatus and more particularly to an improved coupling between a tool head and a drive unit.

BACKGROUND OF THE INVENTION

During a teeth-cleaning operation, the usual final step is to polish the teeth with a rotating tool and a mild abrasive. Due to more stringent hygienic requirements, it is now common practice to utilize a disposable plastic tool head which contains a drive shaft and a rubber polishing element, both of which are rotatably mounted in an angled sleeve. The tool head is connected to a normally non-disposable hand-held unit for supporting and driving the tool head. The driving power unit is the same unit which is used to drive other tool heads of the nondisposable type and hence is a relatively durable, substantial unit capable of handling this variety of tool heads.

Most tooth cleaning operations are performed by a dental hygienist, and a majority of these are women who find the all-purpose power units uncomfortable to handle.

In view of the forgoing it is believed that a need exists for a power unit that is specifically designed for use with disposable tool head polishing units. A key component of that unit is a low cost but reliable coupling to the disposable tool head.

Some drive units, particularly those used in Europe, do not mate with the disposable polishing heads currently being used in the United States. Moreover, most tooth cleaning and polishing operations outside of the U.S. were being performed by dentists rather than dental hygienists. However, in recent years, this situation is changing so that more and more dental hygienists are performing those tasks. Thus, a need also exists for a coupling assembly that will fit a power unit and the disposable polishing head.

SUMMARY OF THE INVENTION

Briefly stated, the invention comprises a simple and inexpensive coupling for attachment to a disposable tool head. The disposable unit employs a plastic power input shaft, and the coupling for driving that shaft utilizes a drive shaft having a tubular end which fits over the plastic shaft. A plurality of balls are captured in sockets within the tubular wall of the drive shaft. The balls protrude into a plastic shaft receiving space in the tubular end of the drive shaft. The end of the plastic shaft fits into the receiving space of the tubular drive shaft, forming an interference fit with the balls. As the shafts are coupled, the balls create axially extending grooves in the exterior of the plastic shaft so that with rotation of the drive shaft the balls rotate the plastic tool head shaft.

The drive shaft is rotatably mounted in a housing, and an end of the housing telescopes onto a sleeve surrounding the plastic input shaft of the disposable head. Thus the housing supports and positions the disposable head as well as rotating its input shaft.

It is a very simple operation for a dental hygienist to push a disposable head onto the end of the drive shaft and its surrounding housing. The coupling between the drive shaft and the input shaft in the disposable head is sufficiently durable and reliable to power the polishing element of the disposable head in that such operation typically only takes a few minutes for a single patient. The head of course can be quickly removed and discarded by pulling it away from the drive shaft and housing. Such procedure is simpler than that employing a chuck requiring rotating elements. Further, the interference ball coupling technique is simple, lightweight and inexpensive. The coupling arrangement can be provided on a separate drive unit containing a power source or it can be mounted on an adapter unit which is attached to a power unit.

BRIEF DESCRIPTION OF THE DRAWINGS

FIG. 1 is an exploded perspective view of a dental tool according to the present invention;

FIG. 2 is an assembled perspective view of the dental tool of FIG. 1;

FIG. 2a is a cross-sectional view showing a preferred drive coupling of the dental tool taken along line 2a—2a of FIG. 2;

DESCRIPTION OF THE PREFERRED EMBODIMENTS

Figure 3:
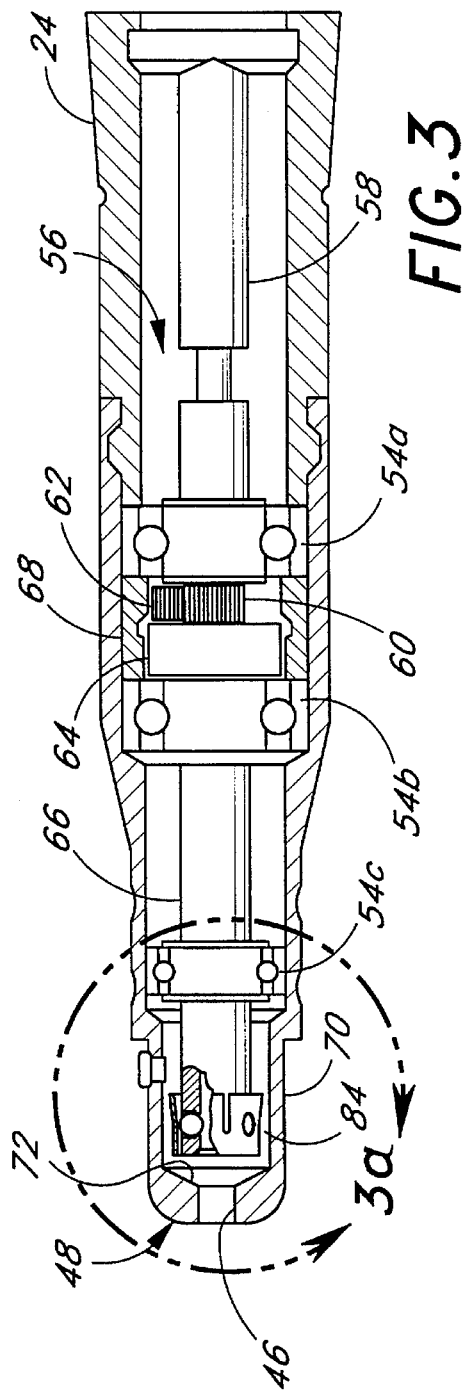
FIG. 3 is a longitudinal sectional view through a housing portion of the dental tool.

FIG. 1 shows a dental tool 20 according to the present invention, comprising a distal disposable tool head 22 and a proximal hand-held housing member 24. Both the tool head 22 and housing member 24 are generally cylindrical in shape and adapted to be coupled together along their axes, as indicated by arrow 26. The assembled dental tool 20 is shown in FIG. 2.

The housing 24 includes a drive assembly for rotating a teeth-cleaning or polishing element 28, and is adapted to couple with a separate drive motor (not shown). Alternatively, a motor may be positioned in the housing. In either case, the teeth-cleaning element 28 generally has a resilient, hollow, frusto-conical shape and has a tube shaft (not shown) adapted to rotate about an axis disposed approximately 90 degrees from the longitudinal axis of the tool head 22. A dentist or hygienist applies a small amount of polishing paste into the hollow teeth-cleaning element 28 and manipulates the hand-held assembly so that the rotating element comes into contact and cleans the surfaces of a patient's teeth.

The disposable tool head 22 is manufactured relatively cheaply and can be discarded after use for sanitary reasons. Typically, the entire disposable tool head 22 is manufactured out of a polymer, such as polypropylene, and has an overall length of approximately two inches. The tool head 22 comprises an outer, generally cylindrical sleeve 32 having a hollow interior through which a tool head shaft 34 extends. The tool head shaft 34 terminates at the distal end at a gear cover 40 containing a first bevel gear 36. The first bevel gear 36 is in mating relationship with a second bevel gear 38 rotatably fixed with respect to the rotating tip 30 and mounted to rotate about an axis disposed 90° with respect to the axis of the tool head shaft 34. Rotation of the shaft 34 thus causes the teeth-cleaning element 28 to spin due to the meshing bevel gears 36, 38 within the gear cover 40.

At a proximal end of the tool head 22, an input end 42 of the tool head shaft 34 extends from an input end 44 of the outer sleeve 32. The input end 42 of the shaft is sized to fit within a through bore entrance 46 of a nose 48 of the housing member 24. The nose 48 comprises a tubular member sized to fit within the input end 44 of the sleeve 32. An anti-rotation pin 50 is aligned with an anti-rotation slot 52 in the sleeve 32 for rotationally locating the tool head 22 with respect to the nose 48. When coupled together, as seen in FIG. 2, the tool head shaft 34 extends completely within the through bore entrance 46, while the nose 48 is covered by the sleeve 32.

Now with reference to FIG. 3, the housing member 24 generally comprises a hollow, somewhat tapered tubular structure having a plurality of bearings 54 mounted therein for supporting a drive shaft assembly 56. From a proximal end to the distal nose 48, the drive shaft assembly 56 comprises a drive shaft 58 keyed to a spur gear 60, which is in meshing engagement with an idler gear 62 mounted for rotation on an off-center shaft (not shown) of a gear plate 64, which is rotatably affixed to an output shaft 66. The drive shaft 58 is journalled within a first bearing 54a and rotates the spur gear 60, which in turn causes the idler gear 62 to rotate about the axis of the spur gear 60, the idler gear being in meshing engagement with a circumscribing ring gear 68. The rotation of the idler gear 62 about the axis of the spur gear 60 causes the gear plate and output shaft 66 to rotate at a much reduced angular velocity from the drive shaft 58. The output shaft 66 is rotatably journalled within a first bearing 54b and a second bearing 54c.

Figure 3A:
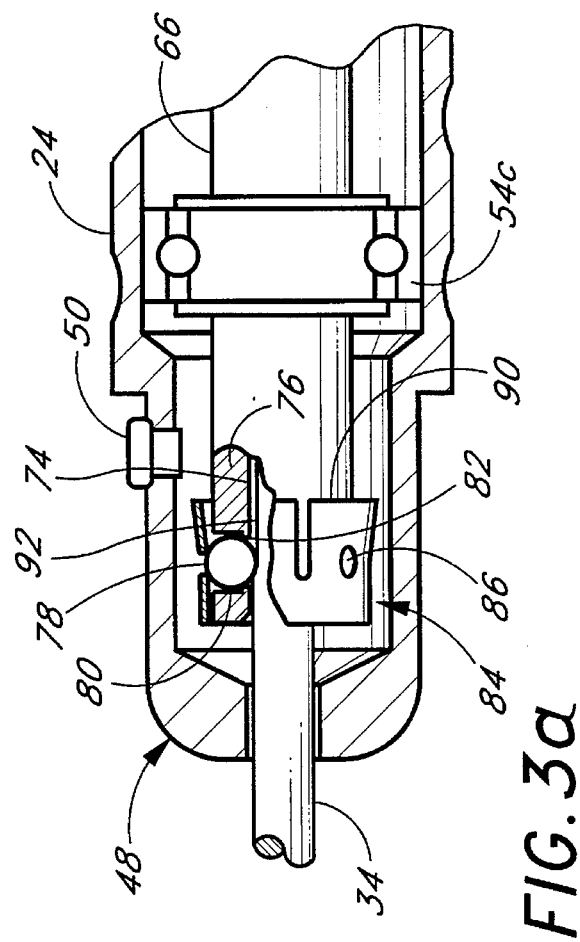
FIG. 3a is a partial sectional view showing a detail of the drive coupling of the dental tool.

The housing member 24 tapers or steps down into a tubular end 70 terminating in the nose 48. The tubular end 70 has an inner diameter sufficient to define a space around the output shaft 66. The output shaft 66 terminates proximate a chamfered transition region 72 leading to the through bore entrance 46. The output shaft 66 is a hollow member having a cylindrical inner wall 74 sized to receive the tool head shaft 34, as seen in FIG. 3a. The output shaft 66 is coupled to the tool head shaft 34, as will be described below, so that rotation of the drive shaft 58 turns the tool head shaft to eventually turn the tooth-cleaning element 28.

Now with specific reference to FIGS. 2a, 3, and 3a, the drive coupling between the output shaft 66 and tool head shaft 34 is described. As mentioned, the output shaft 66 is hollow and generally formed by a tubular wall 76 having an inner cylindrical wall 74. A plurality of circumferentially spaced balls 78 are positioned within holes or sockets 80 extending from an outer surface of the tubular wall 76 to the inner wall 74. In the preferred embodiment, there are preferably three sockets 80 retaining balls 78 therein, but there may be more or less as desired. The sockets 80 are preferably formed as cylinders having a diameter slightly greater than the balls 78. The balls 78 are prevented from falling into the interior of the output shaft 66 by shoulder portions 82 in the sockets 80 having a diameter slightly smaller than the balls 78. The sockets 80 may thus be formed by forming a first hole having the diameter of the shoulder portion 82 and then forming a cylindrical cavity from the exterior of the tubular wall 76 almost entirely through to the inner wall 74 to form the shoulder portions. The diameter of the shoulder portions 82 is such that a ball 78 may extend slightly into the cylinder created by the inner wall 74.

The balls 78 are retained within the sockets 80 by an outer, tubular spring clip or retainer 84. The retainer 84 includes a plurality of locating holes 86 of the same number and spacing as the balls 78 around the output shaft 66. Each locating hole 86 is disposed approximately midway around the circumference of the retainer 84 between a pair of slits 88, each pair of slits 88 defining a resilient arm 90 of the retainer. Thus, in the preferred embodiment, there are three slits 88 defining three resilient arms 90 having centered locating holes 86 therein. Depending on the material and the dimensions for the retainer, the slits could be eliminated.

The inner diameter of the retainer 84 is sized so that the balls 78 are forced to the inner end of the sockets 80 against the shoulder portions 82. Each ball 78 thus extends a short distance into the inner cylinder of the output shaft 66, as best seen in FIG. 2a. Because the tool head shaft 34 is sized approximately equal to the diameter of the inner wall 74, the balls 78 create an interference when the tool head shaft is inserted within the output shaft 86. More specifically, and as seen in FIG. 3a, pushing the tool head shaft 34 into the end of the output shaft 66 causes the balls 78 to form axial grooves 92 in the softer tool head shaft. The balls 78 are preferably formed of hardened steel or other similarly hard material that is capable of deforming the softer tool head shaft 34. Also, the circular retainer 84 is formed of a sufficient wall thickness and material strength to withstand the outward forces exerted on the balls 78 by the inserted tool head shaft 34. Thus, once the disposable tool head 22 is pressed onto the housing member 24 the full extent so that the anti-rotation pin 50 fits within the anti-rotation slot 52, the tool head shaft 34 will be rotatably coupled to the output shaft 66 by way of the interference fit within the balls 78. The balls 78 reside within the axial grooves 92 to provide a certain amount of torsional coupling strength between the output shaft 66 and tool head shaft 34. The torsional coupling strength thus formed need not be substantial, but is sufficient for the teeth-polishing application, as well as similar dental applications.

Figure 4:
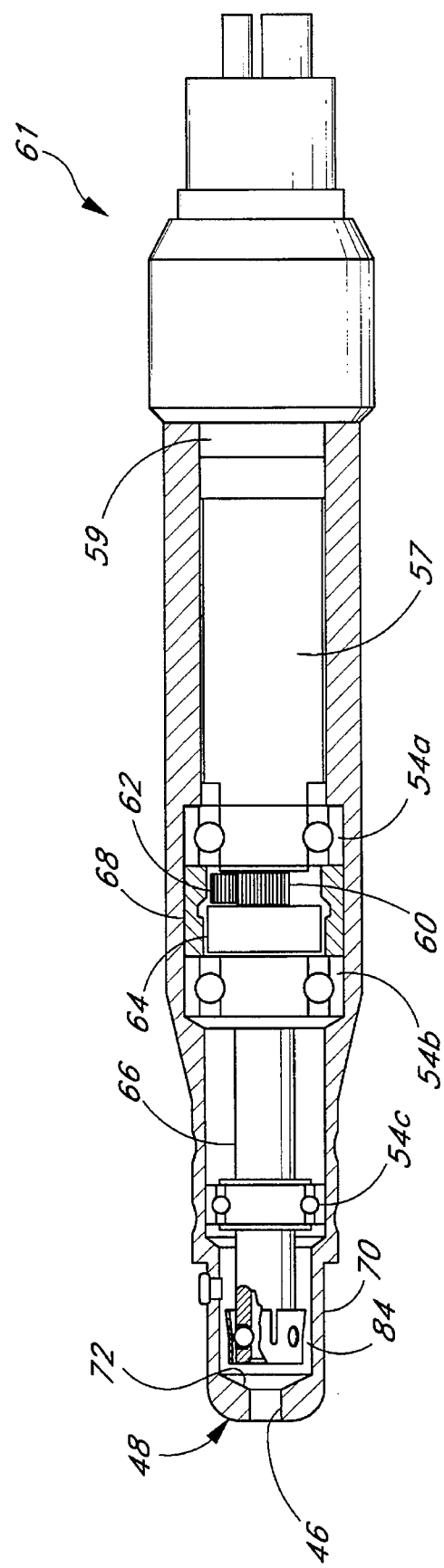
FIG. 4 is a cross-sectional view of a tool including a motor in the hand held housing.

FIG. 4 is similar to FIG. 3, but instead of the housing 24 being adapted to join to a power unit, a small air motor schematically indicated at 57 is positioned in the housing. Schematically illustrated at 59 is an air distributor, with numeral 61 indicating the overall power head assembly.

Although this invention has been described in terms of certain preferred embodiments, other embodiments that are apparent to those of ordinary skill in the art are also within the scope of this invention.

What is claimed is:

1. A dental tool, comprising:

a disposable tool head including an outer sleeve and a shaft rotatably mounted within the sleeve to rotate an element to be applied against a patient's teeth, an input end of said shaft being concentrically positioned in an input end of said sleeve; and a housing having a nose on one end which mates with the input end of said sleeve to support the tool head, an output shaft rotatably mounted in said housing, said output shaft having a tubular end which fits over the input end of said tool head shaft, a plurality of circumferentially spaced balls supported within said nose, said balls being supported with their radially inner surfaces protruding beyond an inner wall of said tubular end, said balls and said input end of said head shaft being arranged and dimensioned so that the input end of said head shaft can be inserted into a space defined by radially inner surfaces of said balls in frictional engagement therewith, said head shaft input end being made of material which is deformable by said balls, and the space defined by said balls is smaller than the diameter of the input end of said head shaft so that a plurality of axially extending grooves are formed in the input end of said shaft when the, input end of said head shaft is inserted into said space, thereby placing said output shaft in driving relation with respect to said head shaft.

2. The tool of claim 1, wherein said tool includes a ring-shaped retainer that fits over said tubular end and captures said balls within sockets in a wall of said tubular wall, the sockets in which said balls are positioned being smaller than the diameter of said balls on the inner surface of said tubular end.

3. The tool of claim 2, wherein said retainer is resilient in the area of said balls so that said balls are resiliently urged radially into engagement with said tool head shaft.

4. A dental tool output shaft assembly for rotating a disposable tool head having an outer sleeve and a shaft rotatably mounted within the sleeve to rotate a cleaning element to be applied against a patient's teeth, said assembly comprising:

a housing;

an output shaft rotatably mounted in said housing, and having a tubular wall which fits over an end of said tool head shaft, said tubular wall having a plurality of circumferentially spaced sockets opening radially to inward and outward surfaces of said wall; and a plurality of circumferentially spaced balls supported within said sockets and protruding inwardly beyond said inner wall surface to define a space so that an end of said head shaft can be inserted into said space in frictional engagement therewith, said balls being made of material which will form circumferentially spaced, axially extending grooves in said shaft when the end of said head shaft is inserted into said space, thereby placing said output shaft in driving relation with respect to said head shaft.

5. The assembly of claim 4, including a ring-shaped retainer that fits over said tubular wall and captures said balls within said sockets, said sockets being smaller than the diameter of said balls on the inner surface of said tubular wall.

6. The assembly of claim 5, wherein said retainer is resilient in the area of said balls so that said balls are resiliently urged radially into engagement with said tool head shaft.

7. The assembly of claim 4, wherein said housing has a nose on one end which mates with an end of said sleeve to support the tool head.

8. The assembly of claim 4, including a motor in said housing connected to said output shaft.

9. A method of coupling a disposable tool head to a hand-held drive housing, comprising:

connecting said head and a nose of said housing to support said tool head; and simultaneously inserting an input end of a tool head shaft into a space defined by a plurality of balls mounted in the walls of a tubular forward end of an output shaft which is rotatably mounted in said housing, said balls and the input end of said head shaft being dimensioned and constructed so that said head shaft interferes with said balls sufficiently to form a plurality of axially extending grooves in the exterior of the drive head shaft thereby rotatably coupling said output shaft to said head shaft.

10. The method of claim 9, wherein said tool head includes a sleeve rotatably supporting said tool head shaft, and said supporting step includes connecting an input end of said sleeve to said nose.

* * * * *